United States Patent [19]

Shewbart et al.

[11] 4,314,090
[45] Feb. 2, 1982

[54] LINEAR ALPHA OLEFIN PRODUCTION

[75] Inventors: William E. Shewbart, Lake Jackson; Steve A. Sims; Billy D. Head, both of Angleton; G. Eldon White, Lake Jackson, all of Tex.

[73] Assignee: The Dow Chemical Company, Midland, Mich.

[21] Appl. No.: 179,348

[22] Filed: Aug. 18, 1980

[51] Int. Cl.$^3$ .............................................. C07C 2/88
[52] U.S. Cl. .................................. 585/328; 585/637
[58] Field of Search ........................................ 585/328

[56] References Cited

U.S. PATENT DOCUMENTS

| | | | |
|---|---|---|---|
| 3,249,648 | 5/1966 | Carter et al. | 585/328 |
| 3,362,975 | 1/1968 | Acciarri et al. | 585/328 |
| 3,502,741 | 3/1970 | Fernald et al. | 585/522 |
| 3,721,719 | 3/1973 | Fernald et al. | 585/522 |

*Primary Examiner*—Curtis R. Davis
*Attorney, Agent, or Firm*—B. G. Colley

[57] ABSTRACT

A method for preparing $C_4$ to $C_{10}$ α-olefins having a major portion $C_6$ α-olefins employing tri alkyl aluminum compounds, e.g., $Al(C_2H_5)_3$ or $Al(C_4H_9)_3$ or mixtures of $Al(C_2H_5)_3$ and $Al(C_4H_9)_3$ as well as the unmixed $C_2$, $C_4$ alkyl aluminum isomers or homologs in the growth step using added ethylene at about 120° C., 500–700 psig, 5–90 minute contact time followed by displacement with $C_2H_4$, $C_4H_8$, or $C_2H_4$ and $C_4H_8$ to free the growth alkyl and regenerate the tri alkyl aluminum compounds. The growth α-olefins are separated with all of the $C_2H_4$ recycled to the growth and displacement steps, and part or all of the $C_4H_8$ recycled to the displacement step.

2 Claims, No Drawings

LINEAR ALPHA OLEFIN PRODUCTION

BACKGROUND OF THE INVENTION

The production of alpha olefins having unbranched carbon skeletal configurations and terminal unsaturation has been practiced for 20 or more years. See for example, Chemical Engineering Progress 58:85-90 (June 1962) and U.S. Pat. No. 3,227,773, dated Jan. 4, 1966. With the advent of the triorganometallic compounds, viz. triethyl and tributyl aluminum, large scale commercial production has occurred. The primary and desired products are the $C_{12}$ to $C_{18}$ $\alpha$-olefins for detergent use and the $C_{26+}$ for synthetic lubricants. The lower carbon atom compounds, viz. $C_6$ to $C_{10}$ have recently found utility in the polymer field and thus they are being recovered from the present day processes in increasing volume. In view of the increasing demand for these lower carbon atom $\alpha$-olefins it would be desirable to have available a process whereby these compounds could be produced to the virtual exclusion of those having more than 10 carbon atoms in their skeletal configuration.

BRIEF DESCRIPTION OF THE INVENTION

It has now been found that employing ethylene, as the olefin feed stock to the growth step and ethylene, butene, or a mixture of ethylene and butylene, which latter is produced in the process, as feed stock to the displacement step of the conventional processes and further employing growth conditions of 100° C. to 140° C., 400 to 800 psig and residence times of 5 to 90 minutes and displacement conditions of 200° C. and above, 100-500 psig and residence time of less than about 2.6 seconds there is obtained a product olefin mixture of $C_2$ to $C_{10}$ where the $C_2$ and $C_4$ olefins are recycled and the $C_6$ to $C_{10}$ are collected as product with $C_6$ olefin being the predominant olefin in the $C_2$-$C_4$ less product.

The theoretical reactions appear to be as follows:

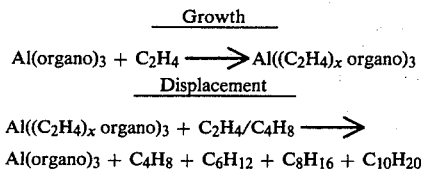

By recycling the $C_2H_4$ and $C_4H_8$ organo portion of the organo metallic compounds the mixture recycled favors, under the conditions of the reaction, the growth to $C_6$, $C_8$ and $C_{10}$ adjuvant with no significant higher adjuvants and sufficient $C_4H_8$ is recycled with no outside source except $C_2H_4$.

DETAILED DESCRIPTION OF THE INVENTION

In accordance with the present invention ethylene gas is fed to a conventional growth reactor maintained at a pressure of from about 400 to about 800 psig and preferably from about 500 to about 700 psig and a temperature of about 100° to about 150° C. and preferably from about 110° to about 120° C. wherein the ethylene reacts with a trialkyl aluminum growth material, viz. triethyl aluminum or tributyl aluminum and preferably a mixture of the two, high in triethyl aluminum content. The reactor is of such size to enable the reactants to be in contact between about 5 and 90 minutes and preferably from about 10 to 20 minutes. Product withdrawn from the growth reactor is cooled to insure the growth products and any unreacted growth material remain in the liquid state yet the ethylene which has not reacted can be separated and returned to the growth reactor as recycle ethylene.

The cooled liquid growth product and any unreacted growth material is then mixed with a displacement gas, ethylene, or butylene or preferably a mixture of ethylene and butylene in a conventional displacement reactor of such size as to displace the material fed in under one second. The displacement gas is preheated to a temperature such that when mixed with the liquid feed stream at the displacement reaction, the temperature will be greater than 250° C. The reactor pressure is maintained at about 100-300 psig.

The displacement product, the olefins and the tri lower alkyl aluminum product, is rapidly quenched to below about 100° C. and fed to the first stage of a separator wherein the displacement gas and the olefins are removed and sent to a second stage separator and the liquid product remaining is directed to a third stage separator. The gaseous products delivered to the second stage separator are further cooled and the displacement gases, ethylene and butylene removed, recompressed, heated, and recycled to the displacement reactor feed stream. The liquid product from the second separation is the desired olefins, in this case $C_4$ to $C_{10}$ $\alpha$-olefins, which may be further separated in its constituent components. The third separator strips any remaining $\alpha$-olefins from the lower alkyl tri aluminum growth material which former are combined with the $\alpha$-olefins from the second separator and the latter, the lower alkyl aluminum compounds sent to a nitrogen padded storage tank for recycle to the growth reactor.

Illustrative of the foregoing description of the process, the conditions and results of four typical examples are shown below wherein all percentages are weight percent.

EXAMPLE 1

Ethylene feed was charged to a carbon steel 50 foot long coiled growth reactor having a 0.5 inch outside diameter and a 0.382 inch inside diameter at a rate of 5.3 grams/minute. A 5 percent by weight solution of triethyl aluminum in n-tetradecane was mixed with the ethylene feed at a rate of 30 ml per minute. Growth conditions were maintained at 500 psig, 125° C. and 5.5 minutes residence time. The growth product was sent to a displacement reactor which consisted of a stainless steel 10 foot long coiled reactor having a 0.125 inch outside diameter and a 0.101 inch inside diameter after flashing off unreacted ethylene. Ethylene displacement gas preheated at 260° C. was added at 8.8 grams/minute to the displacement reactor. Displacement conditions were 210 psig, 245° C., and 1.1 seconds residence time. The displacement product was quenched immediately, and ethylene and butene were flashed overhead in a separator. The liquid bottoms were sent to another separator where the $C_6$-$C_{10}$ linear alpha olefin product was flashed off the aluminum alkyl catalyst under vacuum. Total product collected in 1.6 hours was 23.6 grams and consisted of 48.9%, butene −1, 31.1% hexene-1, 16.4% octene-1, and 3.5% $C_{10}$-$C_{14}$ alpha olefins.

EXAMPLE 2

Following the procedures of Example 1, ethylene was charged to the 50 ft. long growth reactor at 6.2 grams/minute. Growth conditions were 700 psig, 130° C. and 6.3 minutes residence time. Ethylene displacement feed rate was 8.9 grams/minute. Displacement conditions were 200 psig, 270° C., and 1.0 second residence time. Total product collected in 2 hours was 63.1 grams, consisting of 39.3% butene-1, 40.5% hexene-1, 14.9% octene-1, and 5.3% $C_{10}$–$C_{14}$ alpha olefins.

EXAMPLE 3

The procedures of Example 1 were repeated using a 100 foot coil reactor. The ethylene feed rate to the 100 ft. long growth reactor was 10.6 grams/minute. Growth conditions were 700 psig, 131° C. and 7.8 minutes residence time. Ethylene feed rate to the displacement reactor was 7.4 grams/minute. Displacement conditions were 220 psig, 255° C., and 0.9 second residence time. Total product collected in this two hour run was 32.7 grams and consisted of 30.8 wt.% butene-1, 30.0% hexene-1, 29.9% octene-1, and 9.4% $C_{10}$–$C_{14}$ alpha olefins.

EXAMPLE 4

Ethylene feed was charged to the 50 foot long growth reactor at 6.4 grams/minute. A 10 percent solution of 60 percent by weight triethyl aluminum and 40 percent by weight tri- n-butyl aluminum in n-tetradecane was mixed with the ethylene feed at a rate of 30 ml/minute. Growth conditions were 710 psig, 130° C., and 7.4 minutes residence time. The displacing gas, consisting of a mixture of 10 percent ethylene and 90 percent butene-1 by weight, was preheated to 250° C. and added to the displacement reactor at 26.0 grams/minute. Displacement conditions were 200 psig, 255° C., and 0.6 second residence time. The total butene-free product collected in one hour was 15.8 grams, consisting of 34.9 percent hexene-1, 44.6 percent octene-1, 17.3 percent decene-1, and 3.2 percent $C_{12}$–$C_{14}$ alpha olefins.

We claim:

1. A process for producing alpha olefins in the range of about 4 to about 10 carbon atoms per molecule which comprises:

(a) feeding ethylene which may be in part in a recycle system derived from a purification of the product of the process, and triethyl or tributyl or mixed tri(ethylbutyl) aluminum compound in the absence of any significant amount of product olefin in the range of 4 to 10 carbon atoms into a growth reaction system maintained at a temperature between about 100 and 140° C. and a pressure of between about 400 to 800 psig for from about 5 to 90 minutes residence time wherein the ratio of $C_2H_4$ to trialkylaluminum compound is at least 5 to 1, respectively, (b) separating the unreacted olefins from the trialkyl aluminum growth product, (c) displacing the alkyl moieties from the trialkyl aluminum growth product by contacting the growth product with $C_2H_4$, $C_4H_8$, or a mixture of $C_2H_4$ and $C_4H_8$ at a temperature of between about 200° C. and 300° C. for between about 0.1 to about 2.5 seconds residence time under elevated pressure 100 to 500 psig, thereby to displace the higher alkyl moieties of the trialkyl aluminum growth product and replace the displaced alkyl growth moieties with $C_2H_4$ and $C_4H_8$, (d) separating the α-olefin products obtained in the displacement step from the tri lower alkyl aluminum products produced on said displacement step, (e) returning the tri lower alkyl aluminum products to step (a), (f) separating the olefins in the gaseous effluent from said displacement products separation step (d), (g) separating the gaseous effluent into its component parts, including $C_2H_4$ and $C_4H_8$, (h) recycling the $C_2H_4$ component to step (a) and/or step (c) and the $C_4H_8$ to step (c), and (i) recovering the $C_4$, $C_6$, $C_8$, and $C_{10}$ α-olefins as product components.

2. In a process for producing alpha olefins having a range of 4 to 10 carbon atoms as the predominate product wherein ethylene is added to an aluminum trialkyl compound in a growth reaction and subsequently the alpha olefins are displaced in a displacement reaction, the improvement which comprises maintaining the growth reaction conditions at a temperature in the range from about 100° to about 140° C., a pressure from about 400 to 800 psig, a residence time from about 5 to 90 minutes, and the weight ratio of ethylene and/or butylene to aluminum trialkyl is in the range from 5 to 1 to 20 to 1.

* * * * *

UNITED STATES PATENT AND TRADEMARK OFFICE
CERTIFICATE OF CORRECTION

PATENT NO. : 4,314,090

DATED : February 2, 1982

INVENTOR(S) : William E. Shewbart; Steve A. Sims; Billy D. Head; and G. Eldon White It is certified that error appears in the above—identified patent and that said Letters Patent is hereby corrected as shown below:

Col. 3, line 47, change the word "system" to --stream--.

Signed and Sealed this

Twenty-second Day of June 1982

[SEAL]

Attest:

Attesting Officer

GERALD J. MOSSINGHOFF

Commissioner of Patents and Trademarks